United States Patent [19]
Senn-Bilfinger

[11] Patent Number: 5,824,687
[45] Date of Patent: Oct. 20, 1998

[54] PYRIDINIUM SALTS AND THEIR USE FOR THE CONTROL OF HELICOBACTER BACTERIA

[75] Inventor: Jörg Senn-Bilfinger, Konstanz, Germany

[73] Assignee: BYK Gulden Lomberg Chemische Fabrik GmbH, Konstanz, Germany

[21] Appl. No.: 537,772

[22] PCT Filed: Apr. 20, 1994

[86] PCT No.: PCT/EP94/01218

§ 371 Date: Oct. 20, 1995

§ 102(e) Date: Oct. 20, 1995

[87] PCT Pub. No.: WO94/24130

PCT Pub. Date: Oct. 27, 1994

[30] Foreign Application Priority Data

Apr. 22, 1993 [CH] Switzerland .............................. 1232/93

[51] Int. Cl.$^6$ ........................ A61K 31/435; C07D 471/04
[52] U.S. Cl. ............................................. 514/300; 546/121
[58] Field of Search .............................. 546/121; 514/300

[56] References Cited

FOREIGN PATENT DOCUMENTS 0033094  8/1981  European Pat. Off. .

OTHER PUBLICATIONS

Keeling et al., Biochemical Pharmacology, vol. 37(11) pp. 2231–2236 (1988).

*Primary Examiner*—Bernard Dentz
*Attorney, Agent, or Firm*—Jacobson, Price, Holman & Stern PLLC

[57] ABSTRACT

8-phenalkoxyimidazo[1,2-a]pyridinium salts are useful for controlling Helicobacter bacteria. Medicament compositions based on such compounds are prepared and used for the noted purpose.

11 Claims, 1 Drawing Sheet

PYRIDINIUM SALTS AND THEIR USE FOR THE CONTROL OF HELICOBACTER BACTERIA

This application is a 371 of PCT/EP94/01218 filed Apr. 20, 1994.

FIELD OF APPLICATION OF THE INVENTION

The invention relates to novel pyridinium salts and their use for the production of medicaments which are to be employed for the treatment of diseases of the stomach and/or intestine, which are caused by Helicobacter bacteria.

1. Prior Art

A large number of European Patent Applications describe differently substituted imidazo[1,2-a]pyridines (e.g. European Patent Applications 0 033 094, 0 068 378, 0 120 589, 0 204 285, 0 228 006, 0 266 890, 0 268 989 and 0 308 917) which are intended to be suitable for the prevention and treatment of ulcerative diseases of the stomach. It is common to the imidazo[1,2-a]pyridines disclosed in the European Patent Applications mentioned that they are not substituted in the 1-position.

2. Description of the Invention

It has now surprisingly been found that the pyridinium salts described below, which in particular differ from the imidazo[1,2-a]pyridines of the prior art by the substituent in the 1-position, are active against Helicobacter bacteria.

The invention thus relates to the compounds of the formula I (see enclosed formula sheet), in which R1 is $C_nH_{2n}$—A, where A is hydrogen (H), 1–4C-alkylcarbonyl, carboxyl (COOH), 1–4C-alkoxycarbonyl, carbamoyl (CONH$_2$), naphthyl, phenyl or phenyl which is substituted by one or two identical or different substituents from the group consisting of halogen, 1–4C-alkyl, phenyl, 1–4C-alkoxy,-cyano, carboxyl (COOH), 1–4C-alkoxycarbonyl, trifluoromethyl and trifluoromethoxy, and n is the number 1, 2, 3 or 4, R2 is 1–4C-alkyl, R3 is hydrogen (H), 1–4C-alkyl, 2–4C-alkenyl, 2–4C-alkynyl, hydroxy-1–4C-alkyl, amino or cyanomethyl, R4 is hydrogen (H), 1–4C-alkyl, 1–4C-alkoxy or halogen, R5 is hydrogen (H), 1–4C-alkyl, 1–4C-alkoxy or halogen, m is the number 1, 2 or 3 and $X^\ominus$ is a suitable anion, and the salts (betaines) of the carboxylic acids, where R1 is not methyl if R2 is methyl, R3 is cyanomethyl, m is the number 1 and R4 and R5 are hydrogen (H).

Where A=hydrogen (H) and n=1, 2, 3 or 4, $C_nH_{2n}$—A is 1–4C-alkyl.

1–4C-alkyl is a straight-chain or branched alkyl radical having 1 to 4 carbon atoms. Examples which may be mentioned are the butyl, isobutyl, sec-butyl, tert-butyl, propyl, isopropyl, ethyl and methyl radicals.

1–4C-alkylcarbonyl is a radical which, in addition to the carbonyl group, contains one of the abovementioned 1–4C-alkyl radicals. The acetyl radical is preferred.

1–4C-alkoxy is a radical which, in addition to the oxygen atom, contains one of the abovementioned 1–4C-alkyl radicals. The methoxy radical is preferred.

1–4C-alkoxycarbonyl is a radical which, in addition to the carbonyl group, contains one of the abovementioned 1–4C-alkoxy radicals. The methoxycarbonyl and ethoxycarbonyl radicals are preferred.

Halogen within the meaning of the present invention is bromine, chlorine or fluorine.

2–4C-alkenyl is a straight-chain or branched alkenyl radical having 2 to 4 carbon atoms. Examples which may be mentioned are the vinyl, 2-butenyl, 3-butenyl and, in particular, the allyl radical.

2–4C-alkynyl is a straight-chain or branched alkynyl radical having 2 to 4 carbon atoms. The propynyl radical may be mentioned as a preferred alkynyl radical.

Suitable anions $X^\ominus$ are in principle all anions, but particularly those anions which are already present anyway in the alkylating agents R1-X needed for the preparation of the compounds I, or those anions which are customarily used in active compounds in medicaments. Examples which may be mentioned are the chloride, bromide, iodide and methylsulfate ion.

Suitable salts of the carboxylic acids are those with suitable bases, a zwitterion (betaine) being formed by the deprotonation. Examples of basic salts which may be mentioned are lithium, sodium, potassium, calcium, aluminum or magnesium salts, the corresponding bases being employed in the preparation of the salt—depending on whether they are mono- or polybasic bases and depending on which salt is desired—in an equimolar ratio or a quantitative ratio differing therefrom.

Compounds which may be emphasized are those of the formula I in which

R1 is $C_nH_{2n}$—A, where

A is hydrogen (H), naphthyl, phenyl or phenyl which is substituted by one or two identical or different substituents from the group consisting of halogen, 1–4C-alkyl, phenyl, 1–4C-alkoxy, cyano, 1–4C-alkoxy-carbonyl, trifluoromethyl and trifluoromethoxy, and n is the number 1, 2, 3 or 4, R2 is 1–4C-alkyl, R3 is 1–4C-alkyl, 3–4C-alkynyl, hydroxy-1–4C-alkyl or cyanomethyl R4 is hydrogen (H), R5 is hydrogen (H), m is the number 1 or 2 and $X^\ominus$ is a suitable anion, where R1 is not methyl if R2 is methyl and R3 is cyanomethyl.

Compounds which may be particularly emphasized are those of the formula I in which R1 is $C_nH_{2n}$—A, where A is phenyl or phenyl which is substituted by one or two identical or different substituents from the group consisting of chlorine, fluorine, methyl, methoxy, cyano, methoxycarbonyl, trifluoromethyl and trifluoromethoxy, and n is the number 1 or 2, R2 is methyl or ethyl R3 is methyl, propynyl, hydroxymethyl or cyanomethyl, R4 is hydrogen (H), R5 is hydrogen (H), m is the number 1 and $X^\ominus$ is a suitable anion.

The invention further relates to a process for the preparation of the compounds according to the invention and their salts. The process comprises reacting compounds of the formula II (see enclosed formula sheet), in which R2, R3, R4, R5 and m have the meanings indicated above, with compounds of the formula III $$R1-X \qquad (III)$$

and, if desired, then converting compounds I obtained into their salts, or, if desired, then liberating the compounds I from salts of the compounds I obtained.

The reaction of the compounds II with the compounds III is carried out in a manner familiar per se to the person skilled in the art in suitable, inert solvents. The following examples serve to illustrate the process according to the invention in greater detail. The abbreviation h stands for hour(s), RT for room temperature, and m.p. for melting point. The compounds and salts of these compounds mentioned in the examples are a preferred subject of the invention.

EXAMPLES 1. 1-Benzyl-8-benzyloxy-2,3-dimethylimidazo[1,2-a]pyridinium bromide

A solution of 2 g of 8-benzyloxy-2,3-dimethylimidazo-[1,2-a]pyridine at 50° C., dissolved in 40 ml of anhydrous acetone, is treated with 2.7 g of benzyl bromide and then heated under reflux for 16 h. The precipitate produced in this process is filtered- off and washed with cold acetone. 3.5 g of the title compound of m.p. 190°–192° C. are obtained.

2. 1-Benzyl-8-benzyloxy-3-cyanomethyl-2-methylimidazo-[1,2-a]pyridinium bromide

The title compound of m.p. 188°–190° C. is obtained analogously to Example 1 by reaction of 8-benzyloxy-3-cyanomethyl-2-methylimidazo[1,2,a]pyridine with benzyl bromide.

3. 8-Benzyloxy-1-(4-fluorobenzyl)-2,3-dimethylimidazo-[1,2-a]pyridinium bromide

The title compound of m.p. 188°–191° C. is obtained by reaction of 8-benzyloxy-2,3-dimethylimidazo[1,2-a]pyridine with 4-fluorobenzyl bromide analogously to Example 1.

4. 8-Benzyloxy-1-(4-methoxycarbonylbenzyl)-2,3-dimethylimidazo[1,2-a]pyridinium bromide The title compound of melting range 177°–188° C. is obtained by reaction of 8-benzyloxy-2,3-dimethylimidazo[1,2-a]pyridine with methyl 4-bromomethylbenzoate analogously to Example 1.

5. 8-Benzyloxy-2,3-dimethyl-1-phenethylimidazo[1,2-a]pyridinium bromide

The title compound of m.p. 173°–176° C. is obtained by reaction of 8-benzyloxy-2,3-dimethylimidazo[1,2-a]pyridine with 2-phenethyl bromide analogously to Example 1.

6. 8-Benzyloxy-3-cyanomethyl-2-methyl-1-phenethylimidazo[1,2-a]pyridinium bromide The title compound of m.p. 202°–205° C. is obtained by reaction of 8-benzyloxy-3-cyanomethyl-2-methylimidazo[1,2-a]pyridine with 2-phenethyl bromide analogously to Example 1.

7. 8-Benzyloxy-2-methyl-1-phenethyl-3-(2-propynyl)imidazo[1,2-a]pyridinium bromide The title compound of melting range 142°–150° C. is obtained by reaction of 8-benzyloxy-2-methyl-3-(2-propynyl)imidazo[1,2-a]pyridine with 2-phenethyl bromide analogously to Example 1.

8. 1-Benzyl-8-benzyloxy-2-methyl-3-(2-propynyl)imidazo[1,2-a]pyridinium bromide

The title compound of m.p. 190°–192° C. is obtained by reaction of 8-benzyloxy-2-methyl-3-(2-propynyl)imidazo[1,2-a]pyridine with benzyl bromide analogously to Example 1.

9. 8-Benzyloxy-2,3-dimethyl-1-(4-methylbenzyl)imidazo[1,2-a]pyridinium bromide

The title compound of m.p. 212°–215° C. is obtained by reaction of 8-benzyloxy-2,3-dimethylimidazo[1,2-a]pyridine with 4-methylbenzyl bromide analogously to Example 1.

10. 8-Benzyloxy-1-(3,5-difluorobenzyl)-2,3-dimethylimidazo[1,2-a]pyridinium bromide The title compound of m.p. 195°–196° C. is obtained by reaction of 8-benzyloxy-2,3-dimethylimidazo[1,2-a]pyridine with 3,5-difluorolbenzyl bromide analogously to Example 1.

11. 8-Benzyloxy-1-(3-trifluoromethylbenzyl)-2,3-dimethylimidazo[1,2-a]pyridinium bromide The title compound of m.p. 187°–189° C. is obtained by reaction of 8-benzyloxy-2,3-dimethylimidazo[1,2-a]pyridine with 3-trifluoromethylbenzyl bromide analogously to Example 1.

12. 8-Benzyloxy-2,3-dimethyl-1-(2-naphthylmethyl)imidazo[1,2-a]pyridinium bromide The title compound of m.p. 195°–197° C. is obtained by reaction of 8-benzyloxy-2,3-dimethylimidazo[1,2-a]pyridine with 2-bromomethylnaphthalene analogously to Example 1.

13. 8-Benzyloxy-1-(3-cyanobenzyl)-2,3-dimethylimidazo[1,2-a]pyridinium bromide

The title compound of m.p. 193°–195° C. is obtained by reaction of 8-benzyloxy-2,3-dimethylimidazo[1,2-a]pyridine with 3-bromomethylbenzonitrile analogously to Example 1.

14. 8-Benzyloxy-1-(4-chlorobenzyl)-2,3-dimethylimidazo[1,2-a]pyridinium bromide

The title compound of m.p. 215°–217° C. is obtained by reaction of 8-benzyloxy-2,3-dimethylimidazo[1,2-a]pyridine with 4-chlorobenzyl bromide analogously to Example 1.

15. 8-Benzyloxy-1-(3,5-dimethylbenzyl)-2,3-dimethylimidazo[1,2-a]pyridinium bromide The title compound of m.p. 205°–207° C. is obtained by reaction of 8-benzyloxy-2,3-dimethylimidazo[1,2-a]pyridine with 3,5-dimethylbenzyl bromide analogously to Example 1.

16. 8-Benzyloxy-1-(3,4-dichlorobenzyl)-2,3-dimethylimidazo[1,2-a]pyridinium bromide The title compound of m.p. 199°–201° C. is obtained by reaction of 8-benzyloxy-2,3-dimethylimidazo[1,2-a]pyridine with 3,4-dichlorobenzyl bromide analogously to Example 1.

17. 8-Benzyloxy-1-(3,5-bis-(trifluoromethyl)benzyl)-2,3-dimethylimidazo[1,2-a]pyridinium bromide The title compound of m.p. 183°–186° C. is obtained by reaction of 8-benzyloxy-2,3-dimethylimidazo[1,2-a]pyridine with 3,5-bis-(trifluoromethyl)benzyl bromide analogously to Example 1.

18. 8-Benzyloxy-1-(4-biphenylmethyl)-2,3-dimethylimidazo[1,2-a]pyridinium bromide The title compound of m.p. 145°–150° C. is obtained by reaction of 8-benzyloxy-2,3-dimethylimidazo[1,2-a]pyridine with 4-bromomethylbiphenyl analogously to Example 1.

19. 8-Benzyloxy-3-cyanomethyl-1,2-dimethylimidazo[1,2-a]pyridinium iodide

The title compound of m.p. 185°–186° C. is obtained by reaction of 8-benzyloxy-3-cyanomethyl-2-methylimidazo[1,2-a]pyridine with methyl iodide analogously to Example 1.

20. 8-Benzyloxy-1,2,3-trimethylimidazo[1,2-a]pyridinium iodide

The title compound of m.p. 218°–219° C. is obtained by reaction of 8-benzyloxy-2,3-dimethylimidazo[1,2-a]pyridine with methyl iodide analogously to Example 1.

21. 8-Benzyloxy-3-cyanomethyl-1,2-dimethylimidazo[1,2-a]pyridinium methosulfate

A solution of 100 mg of 8-benzyloxy-3-cyanomethyl-2-methylimidazo[1,2-a]pyridine in 3 ml of dry acetone is treated with 45 mg of dimethyl sulfate and stirred at RT for 16 h. The precipitate formed in this process is filtered off, washed with a little diethyl ether and dried. 90 mg of the title compound of m.p. 185°–187° C. are obtained.

22. 8-Benzyloxy-1-(4-trifluoromethylbenzyl)-2,3-dimethylimidazo[1,2-a]pyridinium bromide The title compound of m.p. 207°–209° C. is obtained by reaction of 8-benzyloxy-2,3-dimethylimidazo[1,2-a]pyridine with 4-trifluoromethylbenzyl bromide analogously to Example 1.

23. 8-Benzyloxy-1-(3,4-difluorobenzyl)-2,3-dimethylimidazo[1,2-a]pyridinium bromide The title compound of m.p. 191°–193° C. is obtained by reaction of 8-benzyloxy-2,3-dimethylimidazo[1,2-a]pyridine with 3,4-difluorobenzyl bromide analogously to Example 1.

24. 8-Benzyloxy-1-(3-chlorobenzyl)-2,3-dimethylimidazo[1,2-a]pyridinium bromide

The title compound of m.p. 183°–185° C. is obtained analogously to Example 23 by reaction with 3-chlorobenzyl bromide.

25. 8-Benzyloxy-1-(4-trifluoromethoxybenzyl)-2,3-dimethylimidazo[1,2-a]pyridinium bromide The title compound of m.p. 148°–151° C. is obtained analogously to Example 23 by reaction with 4-trifluoromethoxybenzyl bromide.

26. 8-Benzyloxy-1-(3-trifluoromethoxybenzyl)-2,3-dimethylimidazo[1,2-a]pyridinium bromide The title compound of m.p. 137°–140° C. is obtained analogously to Example 23 by reaction with 3-trifluoromethoxybenzyl bromide.

27. 8-Benzyloxy-1-(3-methylbenzyl)-2,3-dimethylimidazo[1,2-a]pyridinium bromide

The title compound of m.p. 180°–182° C. is obtained analogously to Example 23 by reaction with 3-methylbenzyl bromide.

28. 8-Benzyloxy-1-(4-t-butylbenzyl)-2,3-dimethylimidazo[1,2-a]pyridinium bromide The title compound of m.p. 200°–202° C. is obtained analogously to Example 23 by reaction with 4-t-butylbenzyl bromide.

29. 8-Benzyloxy-2-methyl-1-(3,5-dimethylbenzyl)-3-(2-propynyl)imidazo[1,2-a]pyridinium bromide The title compound of m.p. 200°–202° C. is obtained by reaction of 8-benzyloxy-2-methyl-3-(2-propynyl)imidazo[1,2-a]pyridine with 3,5-dimethylbenzyl bromide analogously to Example 1.

30. 8-Benzyloxy-1-(4-cyanobenzyl)-2,3-dimethylimidazo[1,2-a]-pyridinium bromide

The title compound of m.p. 143°–147° C. is obtained by reaction with 4-cyanobenzyl bromide analogously to Example 23.

31. 8-Benzyloxy-2,3-dimethyl-1-(2,4-dimethylbenzyl)imidazo[1,2-a]-pyridinium chloride The title compound of m.p. 192°–195° C. is obtained analogously to Example 23 by reaction with 2,4-dimethylbenzyl chloride.

32. 8-Benzyloxy-2,3-dimethyl-1-(2,5-dimethylbenzyl)imidazo[1,2-a]pyridinium chloride The title compound of m.p. 197°–200° C. is obtained analogously to Example 23 by reaction with 2,5-dimethylbenzyl chloride.

33. 8-Benzyloxy-2,3-dimethyl-1-(3,5-dimethylbenzyl)imidazo[1,2-a]pyridinium chloride The title compound of m.p. 168°–173° C. is obtained analogously to Example 23 by reaction with 3,5-dimethylbenzyl chloride.

34. 8-Benzyloxy-1-ethyl-2,3-dimethylimidazo[1,2-a]pyridinium bromide

The title compound of m.p. 193°–195° C. is obtained analogously to Example 23 by reaction with ethyl bromide.

35. 8-Benzyloxy-1-n-propyl-2,3-dimethylimidazo[1,2-a]pyridinium bromide

The title compound of m.p. 206°–209° C. is obtained analogously to Example 23 by reaction with 1-bromopropane.

36. 8-Benzyloxy-1-n-butyl-2,3-dimethylimidazo[1,2-a]pyridinium bromide

The title compound of m.p. 172°–174° C. is obtained analogously to Example 23 by reaction with 1-bromobutane.

37. 2,3-Dimethyl-1-(3,5-dimethylbenzyl)-8-(2-phenethoxy)imidazo[1,2-a]pyridinium bromide The title compound of m.p. 198°–200° C. is obtained analogously to Example 1 by reaction of 2,3-dimethyl-8-(2-phenethoxy)imidazo[1,2-a]pyridine with 3,5-dimethylbenzyl bromide.

38. 8-Benzyloxy-1-(3,5-dimethylbenzyl)-2-methylimidazo[1,2-a]pyridinium bromide

The title compound of m.p. 195°–197° C. is obtained analogously to Example 23 by reaction with 3,5-dimethylbenzyl bromide.

39. 8-Benzyloxy-2-ethyl-3-methyl-1-(3,5-dimethylbenzyl)imidazo[1,2-a]pyridinium bromide The title compound of m.p. 214°–216° C. is obtained analogously to Example 1 by reaction of 8-benzyloxy-2-ethyl-3-methylimidazo[1,2-a]pyridine with 3,5-dimethylbenzyl bromide.

40. 8-Benzyloxy-2-ethyl-3-hydroxymethyl-1-(3,5-dimethylbenzyl)imidazo[1,2-a]-pyridinium bromide The title compound of m.p. 208°–210° C. is obtained analogously to Example 1 by reaction of 8-benzyloxy-2-ethyl-3-hydroxymethylimidazo[1,2-a]pyridine with 3,5-dimethylbenzyl bromide.

41. 8-Benzyloxy-1-(3-methoxycarbonylbenzyl)-2,3-dimethylimidazo[1,2-a]pyridinium bromide The title compound of m.p. 150°–154° C. is obtained analogously to Example 23 by reaction with 3-methoxycarbonylbenzyl bromide.

42. 8-Benzyloxy-1-(3-methoxybenzyl)-2,3-dimethylimidazo[1,2-a]pyridinium chloride The title compound of m.p. 144°–148° C. is obtained analogously to Example 23 by reaction with 3-methoxybenzyl chloride.

43. 8-Benzyloxy-1-(3,4-dimethylbenzyl)-2,3-dimethylimidazo[1,2-a]pyridinium chloride The title compound of m.p. 196°–201° C. is obtained analogously to Example 23 by reaction with 3,4-dimethylbenzyl chloride.

Industrial Utility

The compounds of the formula I in which R1, A, n, R2, R3, R4, R5, m and $X^\ominus$ have the meaning indicated above, and their salts, have useful pharmacological properties which make them industrially utilizable. In particular, they have an antiulcerogenic activity and a marked activity against Helicobacter bacteria. Moreover, the compounds according to the invention are distinguished by a high selectivity of action, the lack of significant side effects and a large therapeutic breadth.

The excellent activity of compounds of the formula I and their salts against Helicobacter bacteria makes possible their use in human medicine as active compounds for the treatment of ulcerative diseases and of illnesses which are based on Helicobacter bacteria.

The invention therefore further relates to a method for the treatment of mammals, in particular humans, suffering from ulcerative diseases and from illnesses which are based on Helicobacter bacteria. The method comprises administering to the ill individual a therapeutically active and pharmacologically tolerable amount of one or more compounds of the formula I and/or their pharmacologically tolerable salts.

The invention additionally relates to the compounds of the formula I and their pharmacologically tolerable salts for administration in the treatment of ulcerative diseases and of illnesses which are based on Helicobacter bacteria.

The invention also comprises the use of compounds of the formula I and their pharmacologically tolerable salts in the preparation of medicaments which are employed for the control of ulcerative diseases and those illnesses which are based on Helicobacter bacteria.

The invention further relates to medicaments for the treatment of ulcerative diseases and for the control of Helicobacter bacteria, which comprise one or more compounds of the general formula I and/or their pharmacologically tolerable salts.

Of the Helicobacter strains against which the compounds of the formula I prove to be active, the strain Helicobacter pylori may be mentioned in particular.

The medicaments are prepared by processes known per se which are familiar to the person skilled in the art. The medicaments employed are the pharmacologically active compounds of the formula I and their salts (=active compounds), either as such, or preferably in combination with suitable pharmaceutical auxiliaries, e.g. in the form of tablets, coated tablets, capsules, emulsions, suspensions, gels or solutions, the active compound content advantageously being between 0.1 and 95%.

The person skilled in the art is familiar with the auxiliaries which are suitable for the desired pharmaceutical formulations on the basis of his expert knowledge. In addition to solvents, gel formers, tablet auxiliaries and other active compound excipients, for example antioxidants, dispersants, emulsifiers, antifoams, flavor corrigents, preservatives, solubilizers, colorants or permeation promoters and complexing agents (e.g. cyclodextrins) can be used.

The active compounds can be administered, for example, parenterally (e.g. intravenously) or, in particular, orally.

In general, in human medicine the active compounds are administered in a daily dose of approximately 0.5 to 50, preferably 1 to 30, mg/kg of body weight, if appropriate in the form of several, preferably 2 to 6, individual doses to achieve the desired result.

Biological Investigations

The compounds according to the invention were investigated with respect to their activity against Helicobacter pylori following the methodology described by Tomoyuki Iwahi et al. (Antimicrobial Agents and Chemotherapy, 1991, 490–496) using Columbia agar (Oxoid) and with a growth period of 4 days. For the compounds investigated, the MIC values shown in the table below resulted in this case (the numbers of the compounds indicated correspond to the numbers of the examples).

| Compound No. | MIC Value (µg/ml) |
|---|---|
| 3 | ≦10 |
| 4 | ≦10 |
| 5 | ≦10 |
| 6 | ≦10 |
| 7 | ≦10 |
| 10 | ≦10 |
| 12 | ≦10 |
| 13 | ≦10 |
| 18 | ≦10 |

I claim:
1. A compound of the formula I

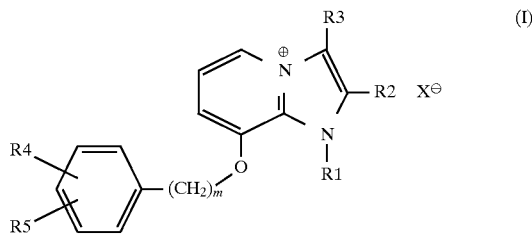

in which
R1 is $C_nH_{2n}$—A, where
A is hydrogen (H), 1–4C-alkylcarbonyl, carboxyl (COOH), 1–4C-alkoxycarbonyl, carbamoyl (CONH$_2$), naphthyl, phenyl or phenyl which is substituted by one or two identical or different substituents from the group consisting of halogen, 1–4C-alkyl, phenyl, 1–4C-alkoxy, cyano, carboxyl (COOH), 1–4C-alkoxycarbonyl, trifluoromethyl and trifluoromethoxy, and
n is the number 1, 2, 3 or 4,
R2 is 1–4C-alkyl,
R3 is hydrogen (H), 1–4C-alkyl, 2–4C-alkenyl, 2–4C-alkynyl, hydroxy-1–4C-alkyl, amino or cyanomethyl,
R4 is hydrogen (H), 1–4C-alkyl, 1–4C-alkoxy or halogen,
R5 is hydrogen (H), 1–4C-alkyl, 1–4C-alkoxy or halogen,
m is the number 1, 2 or 3 and
X$^\ominus$ is a suitable anion,
and the a salt (betaine) of a carboxylic acid thereof, where R1 is not methyl when R2 is methyl, R3 is cyanomethyl, m is the number 1 and R4 and R5 are hydrogen (H).

2. A compound of formula I as claimed in claim 1, in which
R1 is $C_nH_{2n}$—A, where
A is hydrogen (H), naphthyl, phenyl or phenyl which is substituted by one or two identical or different substituents from the group consisting of halogen, 1–4C-alkyl, phenyl, 1–4C-alkoxycarbonyl and trifluoromethyl and
n is the number 1 or 2,
R2 is 1–4C-alkyl,
R3 is 1–4C-alkyl, 3–4C-alkynyl or cyanomethyl,
R4 is hydrogen (H),
R5 is hydrogen (H),
m is the number 1 and
X$^\ominus$ is a suitable anion,
where R1 is not methyl when R2 is methyl and R3 is cyanomethyl.

3. A compound of formula I as claimed in claim 1, in which

R1 is $C_nH_{2n}$—A, where

A is hydrogen (H), naphthyl, phenyl or phenyl which is substituted by one or two identical or different substituents from the group consisting of halogen, 1–4C-alkyl, phenyl, 1–4C-alkoxy, cyano, 1–4C-alkoxycarbonyl, trifluoromethyl and trifluoromethoxy, and n is the number 1, 2, 3 or 4, R2 is 1–4C-alkyl, R3 is 1–4C-alkyl, 3–4C-alkynyl, hydroxy-1–4C-alkyl or cyanomethyl R4 is hydrogen (H), R5 is hydrogen (H), m is the number 1 or 2 and $X^\ominus$ is a suitable anion, where R1 is not methyl when R2 is methyl and R3 is cyanomethyl.

4. A compound of formula I as claimed in claim 1, in which

R1 is $C_nH_{2n}$—A, where

A is phenyl or phenyl which is substituted by one or two identical or different substituents from the group consisting of chlorine, fluorine, methyl, methoxy, cyano, methoxycarbonyl, trifluoromethyl and trifluoromethoxy, and n is the number 1 or 2, R2 is methyl or ethyl R3 is methyl, propynyl, hydroxymethyl or cyanomethyl, R4 is hydrogen (H), R5 is hydrogen (H), m is the number 1 and $X^\ominus$ is a suitable anion.

5. A process for the preparation of a compound of formula I as claimed in claim 1, or a salt thereof, which comprises reacting a compound of formula II

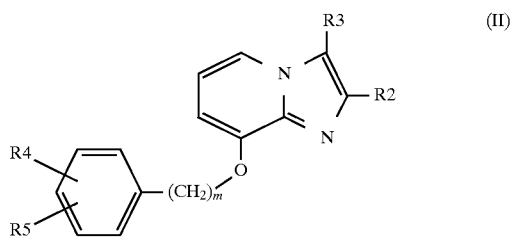

in which R2, R3, R4, R5 and m have the meanings indicated in claim 1, with a compound of formula III

R1—X  (III)

in which R1 has the meaning indicated in claim 1 and X is the covalently bonded form of the suitable anion $X^\ominus$, and, if desired, then converting the compound I obtained into a salt, or, if desired, then liberating the the compound I from a salt of the compound I obtained.

6. A medicament composition comprising a suitable carrier and, as active component, an effective amount of a compound of claim 1 or a pharmacologically-tolerable salt thereof.

7. A method of treating a mammal afflicted with an illness caused by Helicobacter bacteria and which comprises administering to such mammal an effective amount of a compound of formula I

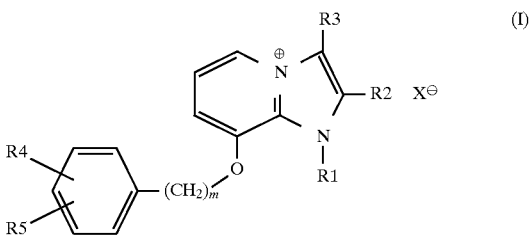

in which

R1 is $C_nH_{2n}A$, where

A is hydrogen (H), 1–4C-alkylcarbonyl, carboxyl (COOH), 1–4C-alkoxycarbonyl, carbamoyl (CONH$_2$), naphthyl, phenyl or phenyl which is substituted by one or two identical or different substitutents selected from the group consisting of halogen, 1–4C-alkyl, phenyl, 1–4C-alkoxy, cyano, carboxyl (COOH), 1–4C-alkoxycarbonyl, trifluoromethyl and trifluoromethoxy, n is the number 1, 2, 3, or 4, R2 is 1–4C-alkyl, R3 is hydrogen (H), 1–4c-alkyl, 2–4C-alkenyl, 2–4C-alkynyl, hydroxy-1–4C-alkyl, amino or cyanomethyl, R4 is hydrogen (h), 1–4C-alkyl, 1–4C-alkoxy or halogen, R5 is hydrogen (H), 1–4C-alkyl, 1–4C-alkoxy or halogen, m is the number 1, 2 or 3 and $X^\ominus$ is a suitable anion, or a pharmacologically-tolerable salt (betaine) of a carboxylic acid thereof.

8. In compounding a medicament composition having an effective amount of an active component for controlling Helicobacter bacteria, the improvement wherein the active component is a compound of claim 1 or a pharmacologically-tolerable salt (betaine) of a carboxylic acid thereof.

9. A method of claim 7 wherein the Helicobacter bacteria are Helicobacter pylori.

10. A method of claim 8 wherein the Helicobacter bacteria are Helicobacter pylori.

11. A method of treating a mammal afflicted with an illness caused by Helicobacter bacteria, which comprises administering to the mammal an effective amount of a pharmacologically-acceptable compound of claim 1.

* * * * *

UNITED STATES PATENT AND TRADEMARK OFFICE
CERTIFICATE OF CORRECTION

PATENT NO. : 5,824,687
DATED : Oct. 20, 1998
INVENTOR(S) : Senn-Bifinger

It is certified that error appears in the above-identified patent and that said Letters Patent is hereby corrected as shown below:

col. 1, line 24, change "Description" to -- Summary --.

col. 1, between lines 28 and 29 insert the following:

Figure 1:
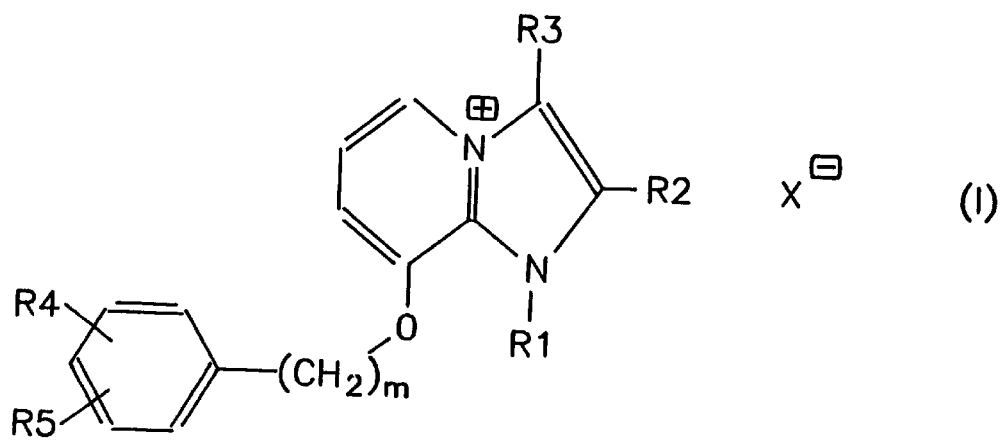
Figure 1 is formula I of the compounds of the subject invintion.
Figure 2:
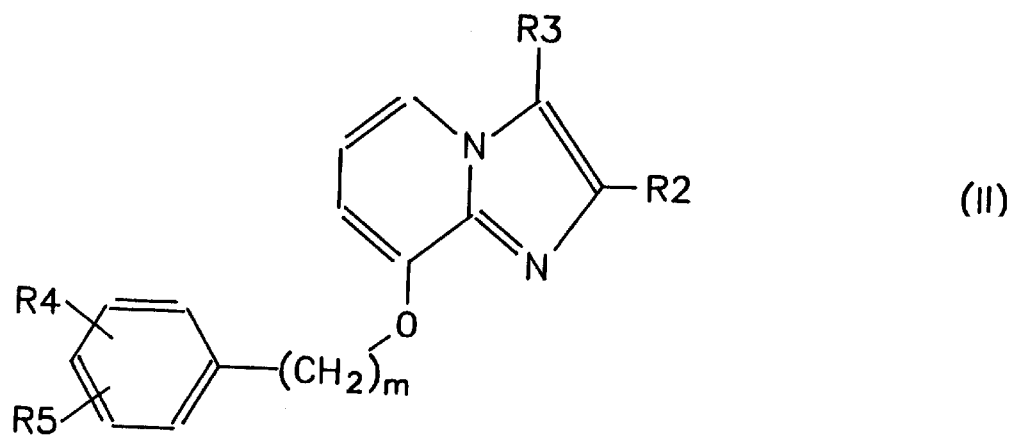
Figure 2 is formula II of starting materials for synthesizing compounds of formula I.

Details -- col. 1, line 29, delete "thus" and "the" (second occurrence).

col. 1, line 30 delete "(see enclosed formula sheet)".

col. 2, line 59 delete "(see enclosed formula sheet)".

Signed and Sealed this

Thirtieth Day of March, 1999

*Attest:*

Q. TODD DICKINSON

*Attesting Officer*   Acting Commissioner of Patents and Trademarks